United States Patent
Biernat et al.

(10) Patent No.: US 7,802,885 B2
(45) Date of Patent: Sep. 28, 2010

(54) IMAGING UNIT FOR OPHTHALMOLOGICAL DEVICES, IN PARTICULAR, FOR FUNDUS CAMERAS AND METHOD FOR THE USE THEREOF

(75) Inventors: Detlef Biernat, Jena (DE); Ingo Koschmieder, Jena (DE); Bernhard Rassow, Hamburg (DE); Thomas Mohr, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 312 days.

(21) Appl. No.: 11/921,702

(22) PCT Filed: Jun. 22, 2006

(86) PCT No.: PCT/EP2006/006002

§ 371 (c)(1),
(2), (4) Date: Dec. 6, 2007

(87) PCT Pub. No.: WO2007/000276

PCT Pub. Date: Jan. 4, 2007

(65) Prior Publication Data

US 2008/0192203 A1    Aug. 14, 2008

(30) Foreign Application Priority Data

Jun. 29, 2005  (DE) ................. 10 2005 030 228

(51) Int. Cl.
*A61B 3/14* (2006.01)
(52) U.S. Cl. ...................................... 351/206
(58) Field of Classification Search ......... 351/205–206, 351/208, 200, 211–214, 221, 246; 600/476, 600/558; 606/4
See application file for complete search history.

(56) References Cited

U.S. PATENT DOCUMENTS 4,070,683 A    1/1978  Altschuler et al.

(Continued)

FOREIGN PATENT DOCUMENTS

DE    281 956    8/1980

(Continued)

OTHER PUBLICATIONS

Klin. Mbl. Augenheilkunde 180, 1982, 286, Littmann, H., "Zur Bestimmung der wahren Größe eines Objektes auf dem Hintergrund des lebenden Auges".

(Continued)

*Primary Examiner*—Jessica T Stultz
*Assistant Examiner*—Mahidere S Sahle
(74) *Attorney, Agent, or Firm*—Frommer Lawrence & Haug LLP

(57) ABSTRACT

A stripe pattern of known distance is imaged on the ocular fundus by the imaging unit for opthalmological devices. This makes it possible to carry out absolute measurements of distances and objects at the ocular fundus with knowledge of the initial values serving as a basis. The imaging unit for opthalmological devices, particularly fundus cameras, according to the invention comprises a device for generating and imaging any, but a known, stripe pattern or line pattern on the retina of an eye to be examined, a camera for recording the stripe pattern or line pattern on the retina, and an evaluating unit for determining the distances on the retina. The imaging unit is constructed in such a way that the stripe pattern or line pattern to be imaged is coupled into the beam path between the opthalmological device and the eye to be examined. The use of an imaging unit of this kind as an accessory to opthalmological devices also expands the possibilities for its use in measurements at the ocular fundus. Although the proposed solution is particularly suited to fundus cameras, it can also be used for other opthalmological device.

7 Claims, 1 Drawing Sheet

U.S. PATENT DOCUMENTS

| | | | |
|---|---|---|---|
| 4,423,931 A * | 1/1984 | Shapiro | 351/206 |
| 4,650,302 A | 3/1987 | Grant | |
| 5,220,360 A | 6/1993 | Verdooner et al. | |
| 5,479,221 A * | 12/1995 | Heine et al. | 351/214 |
| 6,276,798 B1 * | 8/2001 | Gil et al. | 351/206 |
| 2002/0085173 A1 | 7/2002 | Schippert et al. | |
| 2002/0091323 A1 | 7/2002 | Dreher | |

FOREIGN PATENT DOCUMENTS

| | | |
|---|---|---|
| DE | 36 21 983 | 1/1988 |
| EP | 1 417 925 | 11/2002 |

OTHER PUBLICATIONS

Adv. Ophthalmol vol. 34, 1977, pp. 116-142; Rassow, B. and Wolf, D., "Die Messung der retinalen Sehschärfe mit dem Laserinterferenzgerät als klinishe Routinemethode".

Invest Ophthalm Vis Sci 24, 1983, pp. 169-174, Kennedy, J. B., Schwartz, B., Takamoto, T., EU, J. K. T., "Interference Fringe Scale for Absolute Ocular Fundus Measurement".

Invest Ophthalm Vis Sci 30, 1989, 2314-2319, Baumbach, P., Rassow, B., Wesemann, W., "Absolute Ocular Fundus Dimensions Measured by Multiple-Beam Interference Fringes".

* cited by examiner

IMAGING UNIT FOR OPHTHALMOLOGICAL DEVICES, IN PARTICULAR, FOR FUNDUS CAMERAS AND METHOD FOR THE USE THEREOF

CROSS-REFERENCE TO RELATED APPLICATIONS

This application claims priority of International Application No. PCT/EP2006/006002, filed Jun. 22, 2005 and German Application No. 10 2005 030 228.9, filed Jun. 29, 2005, the complete disclosures of which are hereby incorporated by reference.

BACKGROUND OF THE INVENTION a) Field of the Invention

The present invention is directed to an imaging unit for ophthalmological devices by which a stripe pattern of known distance is imaged on the ocular fundus. In this way, with knowledge of the initial values serving as basis, it is possible to carry out absolute measurements of distances and objects at the fundus.

b) Description of the Related Art

The absolute size of an object can be calculated from an image of the fundus only when all of the geometric-optical data of the camera and particularly of the eye are known. While the axial length and radius of curvature of the cornea of the eye can be determined with relatively little expenditure using standardized devices, the measurement of the values of the refractive power of the rear surface of the cornea, the depth of the anterior chamber, the lens thickness, the refractive power of the lens and the ametropia, which are likewise necessary for an exact calculation, is only possible with a great expenditure and limited accuracy.

The nomogram developed by Littmann [1], from which the desired data can be determined approximately with knowledge of the ametropia and the curvature of the cornea, is of some help. This method, which is rather opaque and has not yet been automated, has not achieved popularity so that there is a need for a simple measuring method which is as automated as possible and which delivers clear measurement results. It should be possible to carry out this measuring method with an auxiliary device which is suitable, for example, for a fundus camera.

Ideally, the images of the fundus camera, the measured values of axial length and corneal curvature and the values of this auxiliary device should be prepared in such a way that the evaluation can be carried out automatically.

Solutions are known from the prior art in which a stripe pattern of known distance is imaged on the ocular fundus for absolute determination of distances and objects at the ocular fundus.

While the solutions of Rassow et al. [2] and Kennedy et al. [3] are still based on two-beam interference, Baumbach et al. [4] in 1989 proposed a laboratory construction in which laser interference fringes were projected on the fundus by a multiple-beam interferometer with Maxwellian imaging.

This solution for an eye examination instrument for measuring topographic data of the fundus of the eye is described in DE 36 21 983 A1. In this solution, high-contrast stripes are generated by a multiple-beam interferometer by Maxwellian projection and are imaged on the retina by a fundus camera. A laser light source whose laser light is reflected into the illumination beam path of the fundus camera is preferably used for generating the interference stripes. The Maxwellian projection guarantees that the imaging quality of the optical media of the eye being examined has no influence on the formation of stripes. The use of multiple interference causes the formation of stripes with a high contrast and the area of laser speckle is sharply restricted. The remaining speckle structure within the stripes is further reduced in contrast when images are recorded by the fundus camera using a strobe light, so that it no longer appears in a distracting manner when taking measurements. Reflections in the fundus recording can be prevented by coupling the laser light into the illumination beam path of the fundus camera.

Through simplified assumptions about the distance of the first principal plane of the eye lens from the corneal vertex and with knowledge of the axial length of the eye and of the curvature of the cornea, the stripe distance on the retina of the eye being examined could be calculated within a close approximation so that a scale was present on the object to be tested.

However, it was disadvantageous in the solutions mentioned above that it was necessary to take substantial actions in the fundus camera employed.

Literature:

[1] Littmann, H., "Zur Bestimmung der wahren Größe eines Objektes auf dem Hintergrund des lebenden Auges", Klin. Mbl. Augenheilkunde 180: 286, 1982
[2] Rassow, B. and Wolf, D., "Die Messung der retinalen Sehschärfe mit dem Laserinterferenzgerät als klinishe Routinemethode", Adv. Ophthalmol 34:116, 1977
[3] Kennedy, J. B., Schwartz, B., Takamoto, T., EU, J. K. T., "Interference Fringe Scale for Absolute Ocular Fundus Measurement", Invest Ophthalm Vis Sci 24: 169, 1983
[4] Baumbach, P., Rassow, B., Wesemann, W., "Absolute Ocular Fundus Dimensions Measured by Multiple-Beam Interference Fringes", Invest Ophthalm Vis Sci 30: 2314, 1989

OBJECT AND SUMMARY OF THE INVENTION

It is the primary object of the present invention to develop a solution for measuring distances and objects at the ocular fundus which enables an automatic evaluation and delivers absolute, clear measured values. The solution should be carried out if possible with an auxiliary device which is suitable, for example, for a fundus camera and can be retrofitted.

According to the invention, this object is met by an imaging unit for ophthalmological devices, including fundus cameras, comprising a device for generating and imaging any, but a known, stripe pattern or line pattern on the retina of an eye to be examined, a camera for recording the stripe pattern or line pattern on the retina, an evaluating unit for determining the distances on the retina, wherein the imaging unit is constructed in such a way that the stripe pattern or line pattern to be imaged is coupled into the beam path between the ophthalmological device and the eye to be examined.

For this purpose, the imaging unit for ophthalmological devices, particularly fundus cameras, in the solution according to the invention comprises a device for generating and imaging any, but a known, stripe pattern or line pattern on the retina of an eye to be examined, a camera for recording the stripe pattern or line pattern on the retina, and an evaluating unit for determining the distances on the retina. The imaging unit is constructed in such a way that the stripe pattern or line pattern to be imaged is coupled into the beam path between the ophthalmological device and the eye to be examined. For this purpose, the imaging unit is connected to the ophthalmological device, for example, a fundus camera. The stripe pattern or line pattern to be imaged can be coupled into the beam path selectively.

The use of an imaging unit of this kind as an accessory to ophthalmological devices also expands the possibilities for its use for absolute measurements at the ocular fundus. In addition, already existing devices can be retrofitted in this way. Although the proposed solution is suitable particularly for fundus cameras, it can also be used for other ophthalmological devices.

In the following, the invention will be described more fully with reference to an embodiment example.

DESCRIPTION OF THE PREFERRED EMBODIMENTS

Figure 1:
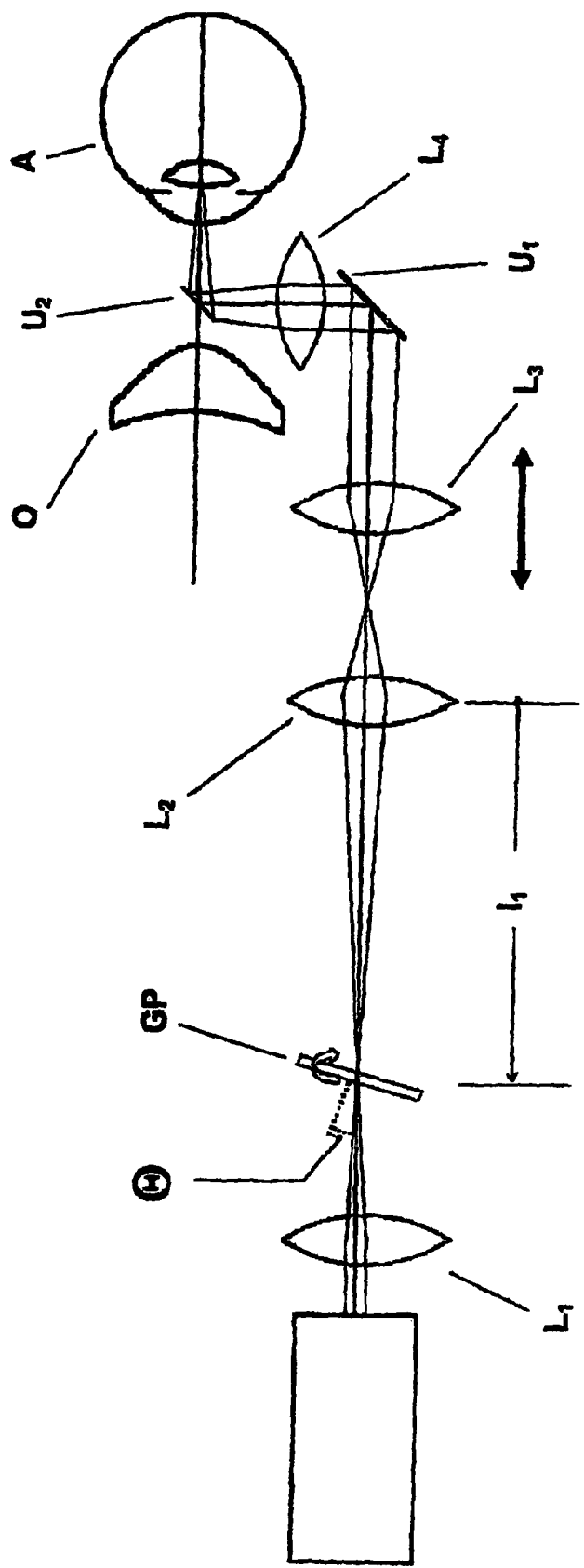
FIG. 1 shows the schematic beam path of the multiple-beam interferometer.

In the solution according to the invention, the imaging unit for ophthalmological devices, particularly fundus cameras, comprises a device for generating and imaging any, but a known, stripe pattern or line pattern on the retina of an eye to be examined, a camera for recording the stripe pattern or line pattern on the retina, and an evaluating unit for determining the distances on the retina. The imaging unit is constructed in such a way that the stripe pattern or line pattern to be imaged is coupled into the beam path between the ophthalmological device and the eye to be examined. For this purpose, the imaging unit is connected to the ophthalmological device, for example, a fundus camera. The stripe pattern or line pattern to be imaged can be coupled into the beam path selectively.

A multiple-beam interferometer having an arrangement for positioning the pattern at the ocular fundus is used as device for generating and imaging a stripe pattern or line pattern. The positioning can be tracked in the eyepiece of the ophthalmological device and/or on a monitor.

The stripe pattern or line pattern can be generated in different ways. In a first design variant, additional optical elements are arranged in the beam path of the multiple-beam interferometer for varying the stripe pattern or line pattern to be imaged.

In another construction which is simple and not susceptible to failure, a plane-parallel glass plate whose tilting angle can be altered for varying the stripe pattern or line pattern to be imaged is arranged in the beam path of the multiple-beam interferometer. But it is also possible to replace the plane-parallel glass plate arranged in the beam path of the multiple-beam interferometer with plane-parallel glass plates of other thickness and accordingly to achieve a variation in the stripe pattern or line pattern to be imaged.

A series of coherent light sources placed closely adjacent to one another whose light bundles are made to overlap and lead to the desired stripe pattern or line pattern in the form of an interference pattern is necessary in order to generate the stripe pattern or line pattern to be imaged. A plane-parallel glass plate which is arranged at an inclination in the beam path and which has on both sides a high reflectance (preferably greater than 90%) for the light wavelength employed is suitable for this purpose.

The plane-parallel glass plate is inserted in the transmission direction and generates light sources of decreasing intensity which in turn lead to a high-contrast stripe structure when approximately 15 to 20 partial bundles are used. In order to accommodate this number of partial bundles within the smallest possible space in the area of the pupil of the eye being examined, the light source points must be arranged as close together as possible. This means that the plane-parallel plate should, when possible, be no thicker than 1.0 mm and the incident angle $\Theta$ of the employed laser light relative to the normal of the plate should be no greater than 10° to 15°. The incident laser beam is focused on the plane-parallel glass plate through a lens in order to make use of the smallest possible homogeneous area of the plate.

In this connection, FIG. 1 schematically shows the beam path of the solution according to the invention in connection with a fundus camera. The point light sources resulting in the vicinity of the plane-parallel glass plate GP are to be imaged in the first principal plane of the lens of the eye A being examined, and a lateral distance of the light points of about 30 µm should be achieved. Accordingly, with 20 light points an area of 0.6 mm diameter in the eye pupil is necessary for irradiation.

The light point density in the lens $L_4$ is then approximately 23 µm and leads to a stripe distance on the retina of approximately one line per degree. Using the above-mentioned data of the glass plate GP, the lateral distance of the light points is about 300 µm. Accordingly, a scale reduction by a factor of about 10 must be achieved by the lens system $L_1$ to $L_4$.

The stripe structure resulting, for example, in a plane in front of the lens $L_2$ will subsequently be imaged on the fundus. In this connection, it must be taken into consideration that the distance $I_2$ from the plane-parallel glass plate GP to this plane cannot be selected optionally. A minimum distance of approximately 100 mm is necessary in order to meet the Fresnel approximation. Moreover, it must be taken into account that the individual point light sources do not lie in a plane perpendicular to the beam direction, but rather so as to be offset axially by the thickness of the glass plate GP to a surface normal. As a result of this, even within the range of validity of the Fresnel approximation, the interference pattern is not sharp in every plane, but rather presents sharp and blurry areas corresponding to the phase displacement of the individual stripes relative to one another. By means of a minimal change in the angle of inclination of the plane-parallel plate, the first sharp imaging of the stripes can strike in the vicinity of the lens $L_2$ which, as field lens, circumscribes the boundary of the bundle by its edge. It should just about be illuminated by means of lens $L_1$. $L_3$ must be finely displaceable axially to align the interferometer. Accordingly, the interferometer can be adjusted by means of changing the incident angle $\Theta$ at the plane-parallel plate and by displacing the lens $L_3$.

While a displacement of the lens $L_3$ influences the position of the focusing plane of the laser beam bundle in the eye A to be examined, varying the incident angle $\Theta$ causes a phase displacement of the individual partial waves of the laser beam bundle relative to one another.

The light bundle generating the stripe pattern or line pattern is coupled into the beam path between the objective O of an ophthalmological device and the eye A being examined by means of a deflecting system $U_1$ and $U_2$, which can comprise either mirrors or splitter plates. For this purpose, the imaging unit is connected to the existing ophthalmological device, e.g., a fundus camera, and the stripe pattern or line pattern to be projected is selectively coupled into the beam path. The size of $U_2$ is given by the angular opening of the beam cone which is about 10°. This results in a measurement area with a diameter of about 2 mm on the ocular fundus in which approximately 10 interference fringes appear which can be used to measure objects of the ocular fundus. Assuming that the splitter mirror is at a distance of about 25 mm from the cornea, and accordingly about 30 mm from the first principal plane of the eye lens, this gives a diameter for $U_2$ of approximately 2 mm.

In a preferred construction, the device for generating and imaging any, but a known, stripe pattern or line pattern radiates linearly polarized light, and a polarization filter is arranged in the observation beam path of the ophthalmological device for suppressing reflections occurring at different media of the eye.

When the polarized beam enters the different media of the eye, a portion of the radiation is reflected at these media transitions. The reflected radiation can lead to troublesome artifacts due to the superposition with the fundus image. Since the reflected beam components have a certain polarization state, they can be reduced or even filtered out by arranging a polarization filter in the observation beam path of the ophthalmological device. The polarization filter is preferably constructed so as to be adjustable and is arranged in such a way that no additional reflections are caused in the observation beam path.

Based on the known stripe pattern or line pattern and the actual settings of the multiple-beam interferometer and/or the measurement values of other ophthalmological devices, the evaluating unit automatically determines the distances on the retina and the determined data and images are displayed, archived and/or transmitted.

The distance between two interference lines on the retina (a) is calculated by the following formula:

$$a = \lambda \cdot n/d \cdot (l_A - l_H)/(l - D_C \cdot l_H/n),$$

where $\lambda$ is the wavelength of the laser light $d/n$ is the distance of the laser foci in the first principal plane of the eye lens $n$ is the refractive index of water $l_A$ is the bulb length $l_H$ is the distance between the corneal vertex and the first principal plane of the eye lens $D_C$ is the refractive index of the cornea.

Apart from the quantities which are fixed by the construction of the multiple-beam interferometer, the values of the refractive index of the cornea and the axial length of the eye are also necessary and must be determined by two additional measurements. The quantity $l_H$ is an empirical quantity which stands for the distance of the cornea from the first principal plane of the eye lens. It is calculated from the data of Gullstrand's eye model and is measured and checked in a randomly selected group of persons. Axial ametropias in the range of +7 to -7 dpt have no influence on the results. With extreme ametropias and particularly with high refractive ametropias, a further correction can be included under certain circumstances, wherein the ametropias should be known to approximately ±7 dpt, but this is also the case in general with higher ametropias.

With respect to the above-mentioned automatic determination of the distances on the retina by the evaluating unit, the measurement values of an autorefractometer can also be included in the determination in addition to the measurement values from interferometers, fundus cameras, ophthalmometers and length measurement instruments. The simplest way is for the position of the eye lens to always be determined at the same time along with the measurement of the axial length of the eye. The distance between the corneal vertex and the principal plane of the lens is then always known. In this case, it is advantageous when all of the measurement data and images of the eye being examined are stored in such a way that the various ophthalmological devices can access these data as needed.

In the proposed technical solution, the Maxwellian projection guarantees that the imaging quality of the optical media of the eye being examined has no influence on the formation of stripes. The use of multiple interference results in the formation of stripes with a high contrast and the area of laser speckle is sharply restricted. The remaining speckle structure within the stripes is further reduced in contrast when fundus images with the interference pattern are recorded by the fundus camera using a strobe light, so that it no longer appears in a distracting manner when taking measurements.

In the solution according to the invention it is particularly advantageous when the imaging unit can be used as an accessory to different ophthalmological devices. In this way, its possible uses can be substantially expanded. Further, already existing devices can be retrofitted in this way.

The use of a plane-parallel glass plate in the beam path of the multiple-beam interferometer makes the imaging unit extremely trouble-proof. The stripe pattern or line pattern to be imaged can be changed in a simple manner by varying the tilting angle of the plane-parallel glass plate.

In a preferred construction, the device for generating and imaging any, but a known, stripe pattern or line pattern can be constructed in such a way that the illumination of the retina can be varied so that a first recording of the retina with a stripe pattern or line pattern is realized by a first camera with little or no illumination of the retina and a second recording of the retina is realized by the first camera or a second camera without a stripe pattern or line pattern with intensive illumination of the retina, and the first and second recordings are combined by the evaluating unit to form a total recording for determining the distances on the retina. The two recordings are preferably made in quick succession.

Since imaging with a known stripe pattern or line pattern is carried out with little or no illumination of the retina, the projected stripes stand out very distinctly from the retina. In contrast, the retina is illuminated intensively for imaging without a stripe pattern or line pattern so that the intensive illumination over-irradiates the projected stripe pattern. In so doing, the second recording with intensive illumination of the retina can also be realized without a stripe pattern or line pattern.

The two images are combined by superimposing them and a high-quality recording of the retina with a clearly visible stripe pattern or line pattern is obtained. The contrast ratio of the stripes to the retina can be adjusted by varying the illumination.

While the foregoing description and drawings represent the present invention, it will be obvious to those skilled in the art that various changes may be made therein without departing from the true spirit and scope of the present invention.

The invention claimed is:

1. An imaging unit for opthalmological devices, including fundus cameras, comprising:
    a device for generating and imaging any known, stripe pattern or line pattern on the retina of an eye to be examined;
    a camera for recording the stripe pattern or line pattern on the retina; and
    an evaluating unit for determining the distances on the retina;
    wherein said imaging unit is constructed in such a way that the stripe pattern or line pattern to be imaged is coupled into the beam path between the opthalmological device and the eye to be examined; and
    wherein plane-parallel glass plates of different thicknesses are arranged in the beam path of a multiple-beam interferometer at defined tilting angles for varying the stripe pattern or line pattern to be imaged.

2. An imaging unit for opthalmological devices, including fundus cameras, comprising:
- a device for generating and imaging any known, stripe pattern or line pattern on the retina of an eye to be examined;
- a camera for recording the stripe pattern or line pattern on the retina; and
- an evaluating unit for determining the distances on the retina;
- wherein said imaging unit is constructed in such a way that the stripe pattern or line pattern to be imaged is coupled into the beam path between the opthalmological device and the eye to be examined; and
- wherein the device for generating and imaging any known, stripe pattern or line pattern is constructed in such a way that the illumination of the retina can be varied so that recordings of the retina with a stripe pattern or line pattern can be realized by one or more cameras with different illumination of the retina and can be combined by the evaluating unit to form a total recording for determining the distances on the retina.

3. The imaging unit for opthalmological devices according to claim 2;
- wherein the evaluating unit automatically determines the distances on the retina based on the known stripe pattern or line pattern, the actual settings of the multiple-beam interferometer and/or the measurement values of other opthalmological devices, and the determined data and images are displayed, archived and/or transmitted.

4. A method for use with the imaging unit for opthalmological devices, comprising the steps of:
- generating any known, stripe pattern or line pattern by a device and imaging said pattern on the retina of an eye to be examined;
- recording the image of said stripe pattern or line pattern on the retina recorded by a camera;
- determining distances on the retina therefrom by an evaluating unit; and
- constructing the imaging unit in such a way that the stripe pattern or line pattern to be imaged is coupled into the beam path between the opthalmological device and the eye to be examined;
- wherein plane-parallel glass plates of different thicknesses are arranged in the beam path of a multiple-beam interferometer at defined tilting angles for varying the stripe pattern or line pattern to be imaged.

5. A method for use with the imaging unit for opthalmological devices, comprising the steps of:
- generating any known, stripe pattern or line pattern by a device and imaging said pattern on the retina of an eye to be examined;
- recording the image of said stripe pattern or line pattern on the retina recorded by a camera;
- determining distances on the retina therefrom by an evaluating unit; and
- constructing the imaging unit in such a way that the stripe pattern or line pattern to be imaged is coupled into the beam path between the opthalmological device and the eye to be examined;
- wherein the device for generating and imaging any known, stripe pattern or line pattern is constructed in such a way that the illumination of the retina can be varied so that a first recording of the retina with a stripe pattern or line pattern is realized by a first camera with little or no illumination of the retina and a second recording of the retina with a stripe pattern or line pattern is realized by a first camera or a second camera with intensive illumination of the retina, and the first recording and second recording are combined to form a total recording by the evaluating unit for determining the distances on the retina.

6. The method according to claim 5;
wherein the two images of the retina are realized within a short time interval.

7. The method according to claim 5;
wherein the second recording of the retina with intensive illumination of the retina can also be realized without a stripe pattern or line pattern.

* * * * *